(12) United States Patent
Chedid

(10) Patent No.: US 8,802,668 B2
(45) Date of Patent: Aug. 12, 2014

(54) HEMATOPOIETIC NEOPLASM CHEMOTHERAPY

(75) Inventor: Marcio Chedid, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 900 days.

(21) Appl. No.: 12/756,213

(22) Filed: Apr. 8, 2010

(65) Prior Publication Data

US 2010/0261712 A1 Oct. 14, 2010

Related U.S. Application Data

(60) Provisional application No. 61/169,094, filed on Apr. 14, 2009.

(51) Int. Cl.
*A61K 31/5517* (2006.01)

(52) U.S. Cl.
CPC .................................. *A61K 31/5517* (2013.01)
USPC ....................................................... 514/220

(58) Field of Classification Search
USPC ....................................................... 514/220
See application file for complete search history.

(56) References Cited

U.S. PATENT DOCUMENTS 5,134,127 A 7/1992 Stella et al.

FOREIGN PATENT DOCUMENTS

| WO | WO 03/076442 A1 | 9/2003 |
| WO | WO 2009/006043 A2 | 1/2009 |
| WO | WO 2009/071620 A1 | 6/2009 |

OTHER PUBLICATIONS

Armstrong, et al., "MLL translocations specify a distinct gene expression profile that distinguishes a unique leukemia," Nature Genetics, 30:41-47 (2002).
Berge, et al., "Pharmaceutical Salts," Journal of Pharmaceutical Sciences, 66(1):1-19 (Jan. 1977).
Coghlan, et al., "Selective small molecule inhibitors of glycogen synthase kinase-3 modulate glycogen metabolism and gene transcription," Chemistry & Biology, 7(10):793-803.
Engler, et al., "Substituted 3-Imidazol[1,2-a]pyridin-3-yl-4 (1,2,3,4-tetrahydro-[1,4]diazepino-[6,7,1-hi]indol-7-yl) pyrrole-2,5-diones as Highly Selective and Potent Inhibitors of Glycogen Synthase Kinase-3," J. Med. Chem, 47:3934-3937 (2004).
Engler, et al., "The development of potent and selective bisarylmaleimide GSK3 inhibitors," Bioorg. Med. Chem. Lett. 15:899-903 (2005).
Forbes, et al., "Cosmic 2005," Br. J. Cancer, 2006, 94(2), 318-22.
Guzman, et al., "Rapid and selective death of leukemia stem and progenitor cells induced by the compound 4-benzyl, 2-methyl, 1,2,4-thiadiazolidine, 3,5, dione (TDZD-8)," Blood, 110(13):4436-4444 (2007).
Holland-Frei Cancer Medicine, 7th Ed., (2006), Table 8-1, Table 8-4 and Table 8-5.
Holmes, et al., "Glycogen Synthase Kinase-3beta Inhibition Preserves Hematopoietic Stem Cell Activity and Inhibits Leukemic Cell Growth," Stem Cells, 26:1288-1297 (2008).
Holmes, et al., "The Role of Glycogen Synthase Kinase-3beta in Normal Haematopoiesis, Angiogenesis and Leukaemia," Current Medicinal Chemistry, 15:1493-1499 (2008).
Martinez, A., "Preclinical efficacy on GSK-3 Inhibitors: Towards a Future Generation of Powerful Drugs," Medicinal Research Reviews, 28(5):773-796 (2008).
Martinez, et al., "First Non-ATP Competitive Glycogen Synthase Kinase 3 beta (GSK-3beta) Inhibitors: Thiadiazolidinones (TDZD) as Potential Drugs for the Treatment of Alzheimer's Disease," J. Med. Chem., 45:1292-1299 (2002).
Martinez, et al., "SAR and 3D-QSAR Studies on Thiadiazolidinone Derivatives: Exploration of Structural Requirements for Glycogen Synthase Kinase 3 Inhibitors," J. Med. Chem., 48:7103-7112 (2005).
Meijer, et al, "GSK-3-Selective Inhibitors Derived from Tyrian Purple Indirubins," Chemistry & Biology, 10:1255-1266 (2003).
Nicholson, et al., "Identification and inhibition of the ICE/CED-3 protease necessary for mammalian apoptosis," Nature, 376, 37-43 (1995).
Ougolkov, et al., "Inhibition of glycogen synthase kinase-3 activity leads to epigenetic silencing of nuclear factor kB target genes and induction of apoptosis in chronic lymphocytic leukemia B cells," Blood, 110(2):735-742 (2007).
Patel, et al., "Glygocen Synthase Kinase-3 and Cancer: Good Cop, Bad Cop?" Cancer Cell, 14:351-353 (2008).
Polychronopoulos, et al., "Structural Basis for the Synthesis of Indirubins as Potent and Selective Inhibitors of Glycogen Synthase Kinase-3 and Cyclin-Depdendent Kinases," J. Med. Chem., 47:935-946 (2004).
Stahl, et al., Handbook of Pharmaceutical Salts: Properties, Selection and Use, (VCHA/Wiley-VCH, 2002).
Toni, F., et al., "A crosstalk between the Wnt and the adhesion-dependent signaling pathways governs the chemosensitivity of acute myeloid leukemia," Oncogene, 25:3113-3122 (2006).
Wang, et al., "Glycogen synthase kinase 3 in MLL leukaemia maintenance and targeted therapy," Nature, 455:1205-1210 (2008).
Relevant excerpts of a Third Party Report on in vitro data (Dec. 2009).
Kulkarni, N., et al., "Changes in Osteoblast, Chondrocyte, and Adipocyte Lineages Mediate the Bone Anabolic Actions of PTH and Small Molecule GSK-3 Inhibitor," Journal of Cellular Biochemistry, vol. 102, pp. 1504-1518 (2007).

(Continued)

*Primary Examiner* — Samantha Shterengarts
(74) *Attorney, Agent, or Firm* — John C. Demeter

(57) ABSTRACT

A method and medicament for treating mixed lineage leukemia; translocated mixed lineage leukemia; translocated mixed lineage leukemia based acute myelogenous leukemia; translocated mixed lineage leukemia based acute lymphoid leukemia; a non-MLL based chronic myeloproliferative disorder, or non-MLL based acute lymphoid leukemia is provided.

1 Claim, No Drawings

(56) References Cited

OTHER PUBLICATIONS

Kulkarni, N., et al., "Orally Bioavailable GSK-3alpha/beta Dual Inhibitor Increases Markers of Cellular differentiation In Vitro and Bone Mass In Vivo," Journal of Bone and Mineral Research, vol. 21, No. 6, pp. 910-920 (2006).

International Search Report and Written Opinion of the International Searching Authority dated Jun. 16, 2010, for corresponding International Patent Application No. PCT/US2010/030315.

HEMATOPOIETIC NEOPLASM CHEMOTHERAPY

Leukemia's, myeloid, lymphoid and mixed lineage, are clonal neoplasms that arise as a result of at least one chromosomal abnormality. These abnormalities result in a change in gene structure and function. Treatment regimens generally comprise several chemotherapeutic agents administered concomitantly or sequentially. Recent advances, such as imatinib mesylate, nilotinib and dasatinib, have improved the time to progression and overall survival in chronic myeloid leukemia patients. Despite these advances, the therapeutic effectiveness of a particular agent, or combination of agents, is frequently not sustained as additional genetic and/or epigenetic abnormalities are acquired. More efficacious chemotherapeutic agents for the treatment of chronic myeloid leukemia and other hematopoietic malignancies are desirable.

Glycogen synthase kinase 3 (GSK3) is a serine/threonine kinase constitutively active in normal resting cells and is regulated through inhibition of its activity. GSK3 is implicated in various signal transduction networks known to regulate a variety of cell functions. Abnormalities in pathways that use GSK3 as a regulator are implicated in disease pathogenesis which has prompted efforts to develop GSK3 specific inhibitors for various therapeutic applications such as non-insulin-dependent-diabetes, Alzheimer's disease and other neurodegenerative disorders, and developmental disorders. Due to its involvement in multiple pathways, suitable potency of GSK3 inhibition is an important factor in the development of inhibitors for therapeutic applications.

Recently, a specific GSK3 inhibitor has been reported to potentiate the effects of specified chemotherapeutic agents at particular solid tumor types, although lacking useful antitumor activity in its own right, WO2009/006043.

It has also been disclosed that GSK3 plays a role in the maintenance of genetically defined translocated mixed lineage leukemia (MLL leukemia). Wang et al., *Nature*, 455, 1205-1210 (2008). This same report also discloses GSK3 inhibition in genetically defined translocated MLL leukemia by specific GSK3 inhibitor compounds. The GSK-3 inhibitor [(3-(2,4-dichlorophenyl)-4-(1-methyl-1H-indol-3-yl)-1H-pyrrole-2,5-dione (SB216763), and GSK-3 Inhibitor IX, (2'Z,3'E)-6-bromoindirubin-3'-oxime ("GSK3-IX") are mentioned as evidencing positive results.

There is a need for leukemia selective chemotherapeutic agents that exhibit per se therapeutic activity, and improved efficacy in the treatment of a leukemia patient with a specific type of leukemia. The GSK3β inhibitor 7-(2,5-dihydro-4-imidazo[1,2-a]-pyridine-3-yl-2,5-dioxo-1H-pyrrol-3-yl)-9-fluoro-1,2,3,4-tetrahydro-2-(1-piperidinyl-carbonyl)pyrrolo[3,2,1-jk][1,4]benzodiazepine evidences selectivity, per se therapeutic activity, and improved efficacy over SB216763 and GSK3-IX, against several types of leukemia.

One aspect of the invention provides a method of treating a patient suffering from mixed lineage leukemia; translocated mixed lineage leukemia; translocated mixed lineage leukemia based acute myelogenous leukemia; translocated mixed lineage leukemia based acute lymphoid leukemia; a non-MLL based chronic myeloproliferative disorder; or a non-MLL based acute lymphoid leukemia comprising administering to a leukemia patient in need of such treatment an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof.

A second aspect of the invention provides a method of treating a patient suffering from mixed lineage leukemia; translocated mixed lineage leukemia; translocated mixed lineage leukemia based acute myelogenous leukemia; or translocated mixed lineage leukemia based acute lymphoid leukemia comprising administering to a leukemia patient in need of such treatment an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof.

A third aspect of the invention provides a method of treating a patient suffering from mixed lineage leukemia comprising administering to a leukemia patient in need of such treatment an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof.

A fourth aspect of the invention provides a method of treating a patient suffering from translocated mixed lineage leukemia comprising administering to a leukemia patient in need of such treatment an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof.

A fifth aspect of the invention provides a method of treating a patient suffering from translocated mixed lineage leukemia based acute myelogenous leukemia comprising administering to a leukemia patient in need of such treatment an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof.

A sixth aspect of the invention provides a method of treating a patient suffering from translocated mixed lineage leukemia based acute lymphoid leukemia comprising administering to a leukemia patient in need of such treatment an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof.

A seventh aspect of the invention provides a method of treating a patient suffering from a non-MLL based chronic myeloproliferative disorder comprising administering to a leukemia patient in need of such treatment an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof.

An eighth aspect of the invention provides a method of treating a patient suffering from non-MLL based acute myelogenous leukemia; erythroleukemia; or chronic myelogenous leukemia comprising administering to a leukemia patient in need of such treatment an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof.

A ninth aspect of the invention provides a method of treating a patient suffering from non-MLL based erythroleukemia comprising administering to a leukemia patient in need of such treatment an effective amount of 7-(2,5-dihydro-4-imidazo[1,2-a]pyridine-3-yl-2,5-dioxo-1H-pyrrol-3-yl)-9- fluoro-1,2,3,4-tetrahydro-2-(1-piperidinylcarbonyl)-pyrrolo[3,2,1-jk][1,4]benzodiazepine or a pharmaceutically acceptable salt or solvate thereof.

A tenth aspect of the invention provides a method of treating a patient suffering from non-MLL based chronic myelogenous leukemia comprising administering to a leukemia patient in need of such treatment an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof.

An eleventh aspect of the invention provides a method of treating a patient suffering from non-MLL based acute myelogenous leukemia comprising administering to a leukemia patient in need of such treatment an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof.

A twelfth aspect of the invention provides a method of treating a patient suffering from non-MLL based acute lymphoid leukemia comprising administering to a patient in need of such treatment an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof.

A thirteenth aspect of the invention provides a method of treating a patient suffering from a non-MLL based JAK2 (+) chronic myeloproliferative disorder comprising administering to a leukemia patient in need of such treatment an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof.

A fourteenth aspect of the invention provides a method of treating a patient suffering from non-MLL based Philadelphia positive chronic myelogenous leukemia comprising administering to a patient in need of such treatment an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof.

A fifteenth aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of mixed lineage leukemia; translocated mixed lineage leukemia; translocated mixed lineage leukemia based acute myelogenous leukemia; translocated mixed lineage leukemia based acute lymphoid leukemia; a non-MLL based chronic myeloproliferative disorder or a non-MLL based acute lymphoid leukemia.

A sixteenth aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of mixed lineage leukemia; translocated mixed lineage leukemia; translocated mixed lineage leukemia based acute myelogenous leukemia; or translocated mixed lineage leukemia based acute lymphoid leukemia.

A seventeenth aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of mixed lineage leukemia.

An eighteenth aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of translocated mixed lineage leukemia.

A nineteenth aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of translocated mixed lineage leukemia based acute myelogenous leukemia.

A twentieth aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of translocated mixed lineage leukemia based acute lymphoid leukemia.

A twenty-first aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of a non-MLL based chronic myeloproliferative disorder.

A twenty-second aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of non-MLL based acute myelogenous leukemia; erythroleukemia; or chronic myelogenous leukemia A twenty-third aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of non-MLL based erythroleukemia.

A twenty-fourth aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of non-MLL based chronic myelogenous leukemia.

A twenty-fifth aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of non-MLL based acute myelogenous leukemia.

A twenty-sixth aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of a non-MLL based JAK2 (+) chronic myeloproliferative disorder.

A twenty-seventh aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of non-MLL based Philadelphia positive chronic myelogenous leukemia.

A twenty-eighth aspect of the invention provides the use of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof for the preparation of a medicament for the treatment of non-MLL based acute lymphoid leukemia.

A twenty-ninth aspect of the invention provides a compound 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or solvate thereof, for use in the treatment of mixed lineage leukemia; translocated mixed lineage leukemia; translocated mixed lineage leukemia based acute myelogenous leukemia; translocated mixed lineage leukemia based acute lymphoid leukemia; a non-MLL based chronic myeloproliferative disorder; or a non-MLL based acute lymphoid leukemia. In a particular embodiment, the leukemia is translocated mixed lineage leukemia based acute myelogenous leukemia; translocated mixed lineage leukemia based acute lymphoid leukemia; non-MLL based chronic myeloproliferative disorder selected from non-MLL based acute myelogenous leukemia, erythroleukemia, or chronic myelogenous leukemia; non-MLL based acute myelogenous leukemia; or non-MLL based chronic myelogenous leukemia.

The compound 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine is taught to be an inhibitor of GSK-3β in WO 03/076442, where it is referred to as 3-(9-fluoro-6-(piperidin-1-yl)carbonyl)-6,7-dihydro-6H-[1,4]diazepino-[6,7,1-hi]indol-1-yl)-4-(imidazo[1,2-a]pyridin-3-yl)-2,5-dioxopyrrole (Example 365, page 113). The two naming conventions described above are taken to be synonymous and each is taken to identify the following structure:

Compound 1

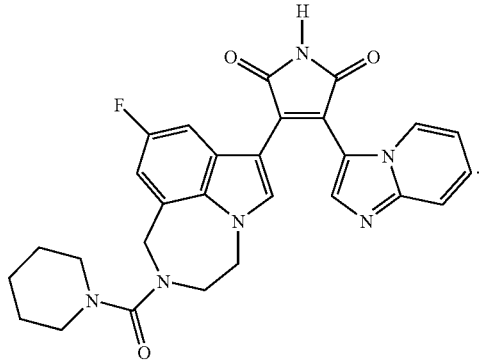

Compound 1 is a base, and accordingly may react with any of a number of inorganic and organic acids to form pharmaceutically acceptable acid addition salts. Pharmaceutically acceptable acid addition salts of the compound of the present invention and common methodology for preparing them are well known in the art. See, e.g., P. Stahl, et al., *Handbook of Pharmaceutical Salts: Properties, Selection and Use*, (VCHA/Wiley-VCH, 2002); S. M. Berge, et al., "Pharmaceutical Salts," *Journal of Pharmaceutical Sciences*, Vol. 66, No. 1, January 1977. Preferred pharmaceutically acceptable acids include HCl, HBr, sulfuric acid and methanesulfonic acid.

Compound 1 forms solvates with, for example, water (hydrate and dihydrate), methanol, and ethanol. A preferred solvate is that formed with ethanol.

As used herein, the term "patient" means mammal; "mammal" means the Mammalia class of higher vertebrates; and the term "mammal" includes, but is not limited to, a human. The preferred patient is a human.

As used herein, the terms "myeloid" and "myelogenous" are used interchangeably. Similarly, "lymphoid" and "lymphogenous" are used interchangeably.

Also as used herein, the term "per se" means independent therapeutic potency. There is no requirement for coadministration of a second active oncologic chemotherapeutic agent to obtain or potentiate leukemia treatment efficacy although such coadministration may be desirable.

There is considerable variability in the degree to which cancer genomes are aberrant at the chromosomal level. Some cancers are characterized by a single signature chromosomal aberration while others have numerous aberrations and very complex karyotypes. In solid tumors, such as epithelial-derived, cytogenetic analyses have identified many structural chromosomal aberrations. This is in contrast to hematopoietic malignancies where a relative few are causally linked and recurrent. The majority of recurrent chromosomal aberrations are found in hematopoietic malignancies in contrast to solid tumors. Deletion and amplification are more characteristic of solid tumors, along with progressive genetic instability and the acquisition of a complex panoply of genomic aberrations in contrast to hematopoietic malignancies.

"Non-MLL based chronic myeloproliferative disorders" are acquired clonal abnormalities of the hematopoietic stem cell and include polycythemia vera, myelofibrosis, essential thrombocytosis, chronic myeloid leukemia, myelodysplastic syndrome and acute myeloid leukemia and includes erythroleukemia. Since the stem cell gives rise to myeloid, erythroid, and platelet cells, qualitative and quantitative changes may be seen in one, two or all those cell lines depending on where in the maturation process from the pluripotent stem cell to a dedicated cell type progenitor stem cell the abnormality occurs. In some disorders (such as chronic myeloid leukemia), specific characteristic chromosomal changes are seen. Chronic myeloproliferative disorders produce characteristic syndromes with defined clinical and laboratory features.

Non-MLL based polycythemia vera causes overproduction of all three hematopoietic cell lines, most prominently erythroid cells. Erythroid production is independent of erythropoietin. A mutation in Janus kinase 2, chromosome band 9p24, (JAK2 (+)), a cell signaling molecule is believed involved in the pathogenesis and is a criteria of diagnosis.

Non-MLL based myelofibrosis is characterized by fibrosis of the bone marrow, splenomegaly, and a leukoerythroblastic peripheral blood picture with teardrop poikilocytosis. In response to bone marrow fibrosis, extramedullary hematopoiesis takes place in the liver, spleen, and lymph nodes. Abnormalities of JAK2 (JAK2 (+)) and its signaling pathway are believed involved in the pathogenesis.

Non-MLL based essential thrombocytosis is characterized by marked proliferation of the megakaryocytes in the bone marrow leading to an elevated platelet count. A high frequency of JAK2 mutations (JAK2 (+)) has been seen in patients and is believed involved in the pathogenesis.

Non-MLL based chronic myeloid leukemia (CML) is characterized by overproduction of myeloid cells. These myeloid cells retain the capacity for differentiation and normal bone marrow function is retained during the early phases. CML is frequently characterized by a specific chromosomal abnormality and specific molecular abnormality. The Philadelphia chromosome is a reciprocal translocation between the long arms of chromosomes 9 and 22. A large portion of 22q is translocated to 9q, and a smaller piece of 9q is moved to 22q. The portion of 9q that is translocated contains abl, a protooncogene that is the cellular homolog of the Ableson murine leukemia virus. The abl gene is received at a specific site on 22q, the break point cluster (bcr). The fusion gene bcr/abl produces a novel protein that differs from the normal transcript of the abl gene in that it possesses tyrosine kinase activity. Evidence that the bcr/abl fusion gene is pathogenic is provided by transgenic mouse models in which introduction of the gene almost invariably leads to leukemia. The presence of this translocation is referred to as Philadelphia positive. In early CML (chronic phase) normal bone marrow function is retained, white blood cells differentiate and, despite some qualitative abnormalities, the neutrophils combat infection normally. CML, however, is inherently unstable and without treatment progresses to an accelerated phase and then an acute or blast phase which is morphologically indistinguishable from conventional acute myeloid leukemia. This progression has been associated with the acquisition of additional genetic and/or epigenetic abnormalities.

Non-MLL based myelodysplastic syndromes are a group of acquired clonal disorders of the hematopoietic stem cell. They are characterized by cytopenia, a hypercellular marrow, and a number of morphologic and cytologic abnormalities. Typically, morphologic abnormalities are present in two or more hematopoietic cell lines. These disorders are typically idiopathic but may be seen after cytotoxic chemotherapy. Although no single specific chromosomal abnormality is seen in myelodysplasia, there are frequent abnormalities involving the long arm of chromosome 5 as well as deletions of chromosomes 5 and 7. Non-MLL based myelodysplasia with a proliferative syndrome are termed chronic myelomonocytic leukemia (CMML).

Non-MLL based acute myeloid leukemia (AML) is a malignancy of one or more myeloid hematopoietic progenitor cells not based upon MLL leukemogenesis. These cells proliferate in an uncontrolled fashion and replace normal bone marrow elements. Although most cases arise with no clear cause, radiation and some toxins are leukemogenic. In addition, a number of chemotherapeutic agents may cause leukemia. The leukemia's seen after toxin or chemotherapy exposure are often associated with abnormalities in chromosomes 5 and 7 or chromosome 11q23. The most common cytogenetic abnormalities causally linked to non-MLL based AML are t(8;21)(q22;q22) affording the AML1/ETO fusion gene; Inv(16)(p13q22) affording the CBFβ/MYH11 fusion gene; t(16;16)(p13;q22), t(15;17)(q21;q11), t(11;17)(q23;q11), t(5;17)(q35;q12-21), t(11;17)(q13;q21), and t(17;17)(q11; q21) affording various RARα containing fusion genes; 5/5q-; -7/7q-; 17p abn or i(17q); del(20q); dmins hsrs; +13; Inv(3) (q21q26), and t(3;3)(q21;q26) affording the Ribophorin/ EVI1 fusion gene. The Auer rod, an eosinophilic needle-like inclusion in the cytoplasm, is pathognomonic of non-MLL based acute myeloid leukemia (AML). Leukemia cells retain properties of the lineages from which they are derived or based. AML cells usually express myeloid antigens such as CD13 or CD33.

Non-MLL based acute lymphoid leukemia (ALL) is a malignancy of the lymphoid hematopoietic progenitor cell not based upon MLL leukemogenesis. As noted above, leukemia cells retain properties of the lineages from which they are derived or based. Non-MLL based ALL cells of B lineage will express lymphoid antigens such as CD19, common to all B cells, and most cases will express CD10 also known as common ALL antigen. Non-MLL based ALL cells of T lineage will usually not express mature T-cell markers, such as CD3, 4, or 8, but will express some combination of CD2, 5, and 7 and do not express surface immunoglobulin. Non-MLL based ALL cells frequently express terminal deoxynucleotidyl transferase (TdT). The most frequent recurrent genetic subtypes include TEL-AML1; BCR-ABL; E2A/PBX1; IgH/ MYC; numerous translocations involving the TCR ab (7q35) or TCR gd (14q11) loci; 1q deletions; SIL-SCL and NOTCH mutations.

Non-MLL based AML has been characterized in several ways. The FAB (French, American, British) classification is based on marrow morphology and histochemistry as follows: acute undifferentiated leukemia (M0), acute myeloblastic leukemia (M1), acute myeloblastic leukemia with differentiation (M2), acute promyelocytic leukemia (APL) (M3), acute myelomonocytic leukemia (M4), acute monoblastic leukemia (M5), erythroleukemia (M6), and megakaryoblastic leukemia (M7). The World Health Organization has sponsored a classification of the leukemia's and other hematologic malignancies that incorporates cytogenetic, molecular, and immunophenotype information, International Classification of Diseases for Oncology, Third edition, Percy et al., 2000.

Non-MLL based ALL may be classified by immunologic phenotype as follows: common, B cell, and T cell. As with non-MLL based AML, certain toxins, radiation and chemotherapeutic agents can cause non-MLL based ALL.

Mixed lineage leukemia (myeloid lymphoid leukemia; MLL) has characteristics of both non-MLL based AML and non-MLL based ALL. MLL specifies a distinct gene expression profile over non-MLL based ALL and non-MLL based AML; Armstrong et. al., *Nature Genetics*, 30, 41-47 (2002). MLL may result from recurrent chromosomal aberrations at chromosome 11 at band q23 (MLL gene), chromosome fusions involving the long arm (q) of chromosome 11 at band q23 with a gene from a different chromosomal region, which may be translocated, or 11q23 may be internally duplicated. Leukemia expressing MLL fusions are frequently aggressive and resistant to chemotherapy. These fusions may translocate resulting in the MLL gene being rearranged. The MLL translocated gene fusions may cause either translocated MLL based AML or translocated MLL based ALL. For example, MLL-AF9 translocated gene fusions frequently, but not exclusively, cause AML (translocated MLL based AML). Other MLL translocated gene fusions associated with translocated MLL based AML include MLL-AF10 and MLL-ELL. A translocated MLL gene fusion associated with translocated MLL based ALL is MLL-AF4.

Extensive catalogues of the cytogenetic aberrations in human cancer have been compiled and are maintained and regularly updated online (see The Mitelman Database of Chromosome Aberrations in Cancer at the US National Cancer Institute (NCI) Cancer Genome Anatomy Project (CGAP) Web site: http://cgap.nci.nih.gov). The database includes chromosomal aberrations for the hematopoietic malignancies of the present invention. The Wellcome Trust Sanger Institute Cancer Genome Project maintains a detailed online "Cancer Gene Census" of all human genes that have been causally linked to tumorigenesis (see http://www.sanger.ac.uk/genetics/CGP/Census) as well as the COSMIC (Catalogue of Somatic Mutations in Cancer) database of somatic mutations in human cancer (see http://www.sanger.ac.uk/genetics/CGP/cosmic). A further source containing abundant information on cytogenetic changes causally linked to leukemia's is the Atlas of Genetics and Cytogenetics in Oncology and Haematology (http://atlasgeneticsoncology.org//Anomalies/Anomliste.html#MDS). These databases also include chromosomal aberrations for the hematopoietic malignancies of the present invention. An alternative source of the Cancer Gene Census database is Holland-Frei Cancer Medicine, $7^{th}$ Ed., (2006), Table 8-1 (See also Table 8-4 for the Most Frequent Recurrent Chromosomal Abnormalities in Myeloid Disorders and Table 8-5 for the Most Frequent Recurrent Genetic Subtypes of B and T Cell ALL) and the COSMIC database is Forbes et al., *Br. J. Cancer,* 2006, 94(2), 318-22.

Diagnosis of hematopoietic malignancies by complete blood counts, bone marrow aspiration and biopsy, immunophenotyping and other tests are known and routinely used. In addition to high resolution chromosome banding and advanced chromosomal imaging technologies, chromosome aberrations in suspected cases of hematopoietic malignancies can be determined through cytogenetic analysis such as fluorescence in situ hybridization (FISH), karyotyping, spectral karyotyping (SKY), multiplex FISH (M-FISH), comparative genomic hybridization (CGH), single nucleotide polymorphism arrays (SNP Chips) and other diagnostic and analysis tests known and used by those skilled in the art.

Beyond the genetic chromosomal aberrations mentioned above, each of the leukemia's may also include epigenetic modifications of the genome including DNA methylation, genomic imprinting, and histone modification by acetylation, methylation, or phosphorylation. An epigenetic modification may play an important role in the malignancy.

The phrase "an effective amount of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinylcarbonyl)-pyrrolo[3,2,1-jk][1,4]benzodiazepine or a pharmaceutically acceptable salt or a solvate thereof" is taken to mean the dosage of Compound 1 or a pharmaceutically acceptable salt or a solvate thereof necessary to either destroy the target leukemia cells or slow or arrest the progression of the leukemia in a patient. Anticipated dosages of Compound 1 or a pharmaceutically acceptable salt or a solvate thereof are in the range of 5 to 600 mg/patient/day. Preferred dosages are anticipated to be in the range of 50 to 400 mg/patient/day. Most preferred dosages are anticipated to be in the range of 100 to 400 mg/patient/day. The exact dosage required to treat a patient will be determined by a physician in view of the stage and severity of the disease as well as the specific needs and response of the individual patient.

The following in vitro and in vivo studies demonstrate the per se therapeutic activity and improved efficacy of Compound 1 against various specific leukemia cell lines.

In Vitro Efficacy Examples

Apoptosis or programmed cell death is characterized by a set of biochemical reactions, one of which is the induction of caspases. Activated caspases are proteases that participate in a cascade of cleavage events that disable key enzymes responsible for cell homeostasis and repair. Caspases 3 and 7 play key effector roles in apoptosis and can be detected and measured by a fluorescent biochemical assay. The increase of Caspase-3/7 activity in cells is directly correlated to apoptotic activity. (D. W. Nicholson, et al., *Nature,* 376, 37-43 (1995)) The Promega Apo-ONE Homogeneous Caspase-3/7 Assay Kit is used (Catalog #G7791). The assay buffer consists of 30 mM HEPES (N-(2-hydroxyethyl)piperazine-N'-(2-ethanesulfonic acid) pH 7.4, 150 mM NaCl, 50 mM KCl, 10 mM $MgCl_2$, 0.4 mM EGTA (ethylene glycol tetraacetic acid), 0.5% Nonidet P40 (octylphenolpoly(ethyleneglycol ether)), 0.1% CHAPS (3-[(3-Cholamidopropyl)dimeth-ylammonio]-1-propanesulfonate hydrate and 10% sucrose, which lyses/permeabilizes cultured cells and a caspase 3/7 substrate, Z-DEVD (Z-Asp(OMe)-Glu(OMe)-Val-Asp(OMe)), coupled to a profluorescent rhodamine 110. When the buffer-substrate mixture is added to a test sample, the cleavage and subsequent removal of the DEVD peptides by caspase 3/7 activity results in intense fluorescence of the rhodamine 110 leaving group, which is detected by excitation at 490 nm. The amount of fluorescent product is proportional to the amount of caspase 3/7 cleavage activity in the sample.

To measure the apoptotic effect of test compounds, tumor cells are plated at $1\times10^4$ cellsper well in 96 well plates and incubated overnight at 37° C., with 5% $CO_2$. Tumor cells are treated with test compound at desired concentrations in triplicate, including untreated/negative control wells. The assay plates are re-incubated for 48 hrs. At the end of the incubation period, a mixture of the assay buffer and substrate is added to each sample well. The fluorescence in each well is measured at an excitation wavelength of 480+/−20 nm and an emission wavelength of 530+/−25 nm. The % increase of caspase activity in treated cells is calculated relative to untreated controls.

Cell viability is determined by the CellTiter-Glo® Luminescent Cell Viability Assay (Promega, Catalog #G7570) which is a method of estimating viable cell number based on quantitation of ATP in metabolically active cells. After cells are lysed, the mono-oxygenation of the substrate luciferin is catalyzed by the enzyme luciferase in the presence of Mg2+, ATP and molecular oxygen, resulting in the generation of a luminescent signal that is proportional to the number of viable cells in the assay wells.

To measure the viability of cells after treatment with compounds, tumor cells are plated at $2\times10^4$ per well in 96 well plates and incubated overnight at 37° C., with 5% CO2. Tumor cells are treated with test compound at desired concentrations in triplicate, including untreated/negative control cells. The assay plates are re-incubated for 48 hrs. At the end of the incubation period, a mixture of lysis assay buffer and substrate is added to each sample well. The luminescence in each well is measured using a microtiter plate luminometer.

MV4;11 is a human acute myeloid leukemia line characterized by the presence of a fusion transcript comprised of the MLL and AF4 genes and by the presence of an internal tandem duplication in the juxtamembrane region of the FLT-3 gene. RS4;11 is a human acute lymphoid leukemia cell line characterized by the presence of a fusion transcript comprised of the MLL and AF4 genes. REH is a human acute lymphoid leukemia (non-T; non-B) cell line characterized by the presence of a fusion transcript comprised of the TEL and AML1 genes. Kasumi 1 is a human acute myeloid leukemia line characterized by the presence of a fusion transcript comprised of the AML1 and ETO genes. K562 is a human chronic myelogenous leukemia cell line characterized by the presence of a fusion transcript comprised of the Bcr and Abl genes. HEL 92.1.7 is a human erythroleukemia cell line characterized by the presence of a V617F mutation in the JAK2 gene. Jurkatt is a human acute T-cell leukemia cell line. Each of the cell lines are obtained from the American Type Culture Collection (ATCC). In the following tables the term "Compound 1" or "Cmpd 1" means 7-(2,5-dihydro-4-imidazo[1,2- a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine. The GSK-3 inhibitor [(3-(2,4-dichlorophenyl)-4-(1-methyl-1H-indol-3-yl)-1H-pyrrole-2,5-dione (SB216763), Sigma-Aldrich is used as a positive comparator control in some experiments. The compound GSK-3 Inhibitor IX, (2'Z,3'E)-6-bromoindirubin-3'-oxime ("GSK3-IX") Calbiochem, is used as a positive control in some experiments. Both SB216763 and GSK3-IX are mentioned in the Wang et al., Nature, 455, 1205-1210 (2008) paper as evidencing positive results. The data in Table 1 are expressed as % increase of caspase 3 activity relative to untreated controls unless otherwise noted.

TABLE 1

Caspase 3 Activity

| Cell line | % Increase in Caspase 3 activity with vehicle | Concentration of Compound 1 (in μM) | % Increase in Caspase 3 after treatment with Cmpd 1 (mean of triplicates) | Concentration of SB216763 (in μM) | % Increase in Caspase 3 after treatment with SB216763 (mean of triplicates) |
|---|---|---|---|---|---|
| MV4; 11 | 0 | 0.010 | 188 | 30 | 83 |
| RS4; 11 | 0 | 0.009 | 111 | 20 | 117 |
| REH | 0 | 0.0007 | 132 | 20 | 113 |
| Kasumi 1 | 0 | 0.370 | 133 | 10 | 27 |
| HEL 92.1.7 | 0 | 0.120 | 284 | 10 | 250 |
| K562 | 0 | 0.0007 | 1057 | 20 | 223 |
| Jurkat | 0 | 0.370 | 140 | 10 | 101 |

The data in Table 1 evidences per se activity by Compound 1 against all cell lines tested and particularly against non-MLL based AML, CML, erythroleukemia and ALL. The data also evidences improved efficacy of Compound 1 over SB216763 against all cell lines tested.

The data in Table 2 are expressed as the estimated concentration required for a reduction in cell viability by 50% (EC50) after treatment with Compound 1 or SB216763.

TABLE 2

Reduction in Cell Viability

| Cell line | Reduction in cell viability after treatment with Cmpd 1 EC50 in μM (mean of triplicates) | Reduction in cell viability after treatment with SB216763 - EC50 in μM (mean of triplicates) | Reduction in cell viability after treatment with GSK3-IX - EC50 in μM (mean of triplicates) |
|---|---|---|---|
| MV4; 11 | 0.082 | 12.6 | 0.2 |
| RS4; 11 | 0.005 | 4.4 | 0.3 |
| REH | 0.006 | 4.2 | 1.1 |
| Kasumi | 0.016 | 10 | 1.2 |
| HEL 92.1.7 | 0.034 | 11.3 | >3.3 |
| K562 | 0.046 | 20 | >3.3 |
| Jurkat | 0.046 | >10 | >3.3 |

The data in Table 2 provides further evidence of per se activity by Compound 1 against all cell lines tested and particularly against non-MLL based AML, CML, erythroleukemia and ALL. The data also evidences improved efficacy of Compound 1 over SB216763 and GSK3-IX against all cell lines tested.

In Vivo Efficacy Experiments

Cultured cells (ATCC) are implanted subcutaneously in the rear flank of female CD-1 nu/nu strain mice which have been acclimated for one week in the animal facility after receipt from the vendor. Mice are randomized into groups of 10 mice per group and treatment begun when the mean tumor volume reaches ~100 mm³. Compound 1 is dosed IV. The tumors are measured 2 times per week by electronic calipers to plot growth curves. Animals are also monitored for fluctuations in body weight and survival.

Three cycles of 5 mg/kg of Compound 1 (injected IV) are given to animals, each cycle separated by 7 days. Animals also receive 6 cycles of Compound 1 (injected IV) given at 0.1 mg/kg and 1 mg/kg, each cycle separated by 3.5 days. 30 mg/kg of the antimetabolite Arabinosylcytosine (injected IP) is given to animals every day for 14 consecutive days as a comparator control. p-value for each treatment group is determined by comparison with the Captisol vehicle control group.

TABLE 3

Antitumor efficacy of Compound 1
in MV4; 11 leukemia xenografts

| Treatment Group | Tumor Volume at day 33 Mean ± Standard Error (mm$^3$) | p-Value |
|---|---|---|
| Captisol vehicle control | 233 ± 23.2 | — |
| Compound 1 (5 mg/kg) administered once a week | 167 ± 11.7 | <0.01 |
| Compound 1 (0.1 mg/kg) administered twice a week | 189 ± 22.3 | — |
| Compound 1 (1 mg/kg) administered twice a week | 154 ± 15 | <0.01 |
| Arabinosylcytosine (30 mg/kg) administered every day for 14 days | 129 ± 11.2 | <0.001 |

The data in Table 3 evidences that the Compound 1 in vitro data demonstrating per se activity and improved efficacy, in the present test in comparison to the antimetabolite Arabinosylcytosine (injected IP), is also seen in vivo.

Synthesis of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine and pharmaceutically acceptable salts and solvates thereof are essentially as described in WO 2009/006043. As described below, synthesis is by common organic chemistry techniques known to one skilled in the art.

Preparation 1

2-imidazo[1,2-a]pyridin-3-yl-acetamide 4,4-Dimethoxy-but-2-enoic acid ethyl ester Add potassium carbonate (16.5 g, 120 mmol) to a solution of dimethoxy acetaldehyde (60% wt. in water) (15 mL, 100 mmol) and triethyl phosphonoacetate (20 mL, 100 mmol) in 210 mL tetrahydrofuran and 30 mL water. Stir the mixture at room temperature for 4 hours. Pour the reaction mixture into diethyl ether (200 mL) and wash with saturated aqueous sodium chloride. Dry the organic phase over sodium sulfate and concentrate under reduced pressure to provide the desired compound as a yellow oil (15.8 g, 90%).
$^1$H-NMR (300 MHz, CDCl$_3$): δ 6.77 (dd, J=15.9, 4.0 Hz, 1H), 6.13 (dd, J=15.9, 1.4 Hz, 1H), 4.95 (dd, J=4.0, 1.4 Hz, 1H), 4.22 (q, J=7.1 Hz, 2H), 3.34 (s, 6H), 1.30 (t, J=7.1 Hz, 3H).

Imidazo[1,2-α]pyridin-3-yl-acetic acid ethyl ester

Heat a mixture of 4,4-dimethoxy-but-2-enoic acid ethyl ester (43.5 g, 250 mmol) and p-toluenesulfonic acid (4.75 g, 25 mmol) in acetonitrile (240 mL) and water (15 mL) at reflux for 2 hours. Cool the reaction mixture to room temperature and add 2-aminopyridine (18.8 g, 200 mmol). Heat the mixture at reflux for 16 hours then cool to room temperature. Dilute the reaction mixture with ethyl acetate (1200 mL) and wash sequentially with saturated aqueous sodium bicarbonate (600 mL×3) and saturated aqueous sodium chloride (600 mL×2). Dry the organic phase over sodium sulfate and concentrate under reduced pressure to provide the desired compound as a brown oil (30 g, 73%).
$^1$H-NMR (300 MHz, CDCl$_3$): δ 8.06 (d, J=6.6 Hz, 1H), 7.63 (d, J=9.1 Hz, 1H), 7.56 (s, 1H), 7.20 (dd, J=8.9, 6.8 Hz, 1H), 6.84 (t, J=6.7 Hz, 1H), 4.17 (q, J=7.3 Hz, 2H), 3.93 (s, 2H), 1.25 (t, J=7.3 Hz, 3H).

Amide Formation

Heat a solution of imidazo[1,2-a]pyridin-3-yl-acetic acid ethyl ester (30 g, 147 mmol) in NH$_3$/MeOH (7 N solution, 250 mL) at 85° C. in a sealed tube for 15 hours. Cool the reaction mixture to room temperature and concentrate under reduced pressure. Treat the residue with dichloromethane, sonicate, and filter the resulting precipitate to provide the desired compound as a yellow solid (8.9 g, 35%).
$^1$H-NMR (300 MHz, DMSO): δ 8.30 (d, J=6.9 Hz, 1H), 7.62 (br s, 1H), 7.54 (d, J=9.0 Hz, 1H), 7.42 (s, 1H), 7.21 (dd, J=7.7, 6.7 Hz, 1H), 7.18 (br s, 1H), 6.91 (t, J=6.8 Hz, 1H), 3.81 (s, 2H).

Preparation 2

9-Fluoro-7-methoxyoxalyl-3,4-dihydro-1H-[1,4]diazepino[6,7,1-hi]indole-2-carboxylic acid tert-butyl ester 2-Dibutoxymethyl-4-fluoro-1-nitro-benzene Heat a solution of 5-fluoro-2-nitro-benzaldehyde (10 g, 59.17 mmol), butanol (20 mL, 219 mmol) and p-toluenesulfonic acid (600 mg, 3.15 mmol) in toluene (200 mL) at reflux for 2 hours in a flask equipped with a Dean-Stark trap. Cool the reaction mixture to room temperature, dilute with ethyl acetate (400 mL), and wash sequentially with saturated aqueous sodium bicarbonate (300 mL×3) and saturated aqueous sodium chloride (300 mL×2). Dry the organic phase over sodium sulfate and concentrate under reduced pressure to provide the desired compound as a pale yellow oil (17 g, 96%).
$^1$H-NMR (300 MHz, CDCl$_3$): δ 7.91 (dd, J=8.9, 4.9 Hz, 1H), 7.53 (dd, J=9.3, 2.9 Hz, 1H), 7.15-7.09 (m, 1H), 6.04 (s, 1H), 3.67-3.50 (m, 4H), 1.63-1.54 (m, 4H), 1.44-1.32 (m, 4H), 0.92 (t, J=7.3 Hz, 6H).

5-Fluoro-1H-indole-7-carbaldehyde

Add vinylmagnesium bromide (1 M in tetrahydrofuran, 85.2 mL, 85.2 mmol) dropwise to a solution of 2-dibutoxymethyl-4-fluoro-1-nitro-benzene (8.5 g, 28.4 mmol) in tetrahydrofuran (250 mL) at −78° C. Warm the reaction mixture −45° C. to −50° C. for 30 minutes, cool to −78° C., and add vinylmagnesium bromide (1 M in tetrahydrofuran, 85.2 mL, 85.2 mmol) drop wise. Warm the reaction mixture to −45° C. to −50° C. for 20 minutes, then add saturated aqueous ammonium chloride (300 mL). Warm the mixture to room temperature and extract with diethyl ether (200 mL×2). Wash the combined organic phases with saturated aqueous sodium chloride (400 mL×2), dry over sodium sulfate, and concentrate under reduced pressure. Dissolve the residue in tetrahydrofuran (100 mL), add 0.5 N HCl (10 mL), and stir for 20 minutes. Dilute the mixture with diethyl ether (200 mL), wash sequentially with saturated aqueous sodium bicarbonate (200 mL×3) and saturated aqueous sodium chloride (200 mL×2). Dry the organic phase over sodium sulfate and concentrate under reduced pressure. Subject the residue to silica gel chromatography, eluting with 5% to 10% ethyl acetate in hexanes to provide the desired compound as a pale yellow solid (2.6 g, 56%).
$^1$H-NMR (300 MHz, CDCl$_3$): δ 10.07 (s, 1H), 10.05 (br s, 1H), 7.62 (d, J=7.6 Hz, 1H), 7.42-7.39 (m, 2H), 6.60 (d, J=5.4 Hz, 1H).

2-[(5-Fluoro-1H-indol-7-ylmethyl)-amino]-ethanol

Add 2-aminoethanol (1.93 mL, 32.0 mmol) followed by acetic acid (2.01 mL, 48.0 mmol) to a solution of 5-fluoro- 1H-indole-7-carbaldehyde (2.6 g, 16.0 mmol) in 1,2-dichloroethane (40 mL). Stir at room temperature for 15 minutes. Add sodium triacetoxyborohydride (4.07 g, 19.2 mmol) portion wise. Stir the reaction mixture at room temperature for 3 hours. Add saturated aqueous sodium bicarbonate (100 mL) slowly followed by 1 N NaOH to pH ~9. Extract with ethyl acetate (100 mL×3). Wash the organic phase with saturated aqueous sodium chloride (200 mL×2), dry over sodium sulfate, and concentrate under reduced pressure to provide the desired compound as a pale yellow solid (3.2 g, 96%).

$^1$H-NMR (300 MHz, CDCl$_3$): δ 9.71 (br s, 1H), 7.24 (d, J=2.7 Hz, 1H), 7.19 (dd, J=9.5, 2.3 Hz, 1H), 6.79 (dd, J=9.8, 2.2 Hz, 1H), 6.49 (dd, J=3.1, 2.2 Hz, 1H), 4.15 (s, 2H), 3.77 (t, J=5.2 Hz, 2H), 2.84 (t, J=5.2 Hz, 2H).

(5-Fluoro-1H-indol-7-ylmethyl)-(2-hydroxy-ethyl)-carbamic acid tert-butyl ester Add a solution of di-tert-butyl dicarbonate (3.63 g, 16.65 mmol) in tetrahydrofuran (40 mL) drop wise to a solution of 2-[(5-fluoro-1H-indol-7-ylmethyl)-amino]-ethanol (3.15 g, 15.14 mmol) in tetrahydrofuran (60 mL) at 0° C. Stir the reaction mixture at room temperature for 2 hours. Add ethyl acetate (200 mL) and wash with saturated aqueous sodium chloride. Dry the organic phase over sodium sulfate and concentrate under reduced pressure to provide the desired compound as a pale yellow oil (4.9 g, >100%).

$^1$H-NMR (300 MHz, CDCl$_3$): δ 10.17 (br s, 1H), 7.27-7.23 (m, 2H), 6.81 (dd, J=9.4, 2.4 Hz, 1H), 6.50 (dd, J=2.9, 2.2 Hz, 1H), 4.67 (s, 2H), 3.72 (br s, 2H), 3.33 (t, J=5.3 Hz, 2H), 1.50 (s, 9H).

Methanesulfonic acid 2-[tert-butoxycarbonyl-(5-fluoro-1H-indol-7-ylmethyl)-amino]-ethyl ester Add triethylamine (4.64 mL, 33.3 mmol) followed by methanesulfonyl chloride (1.29 mL, 16.65 mmol) to a solution of (5-fluoro-1H-indol-7-ylmethyl)-(2-hydroxyethyl)-carbamic acid tert-butyl ester (4.9 g, assume 15.14 mmol) in dichloromethane (70 mL) at 0° C. Stir the reaction mixture for 30 minutes at 0° C. Dilute with ethyl acetate (200 mL), wash with sequentially with saturated aqueous sodium bicarbonate (200 mL×3) and saturated aqueous sodium chloride (200 mL×2). Dry the organic phase over sodium sulfate and concentrate under reduced pressure to provide the desired compound as a yellow brown oil (5.9 g, >100%).

$^1$H-NMR (300 MHz, CDCl$_3$): δ 10.07 (br s, 1H), 7.28-7.2 (m, 2H), 6.83 (dd, J=9.3, 2.3 Hz, 1H), 6.50 (dd, J=2.9, 2.2 Hz, 1H), 4.67 (s, 2H), 4.17 (t, J=5.5 Hz, 2H), 3.51 (t, J=5.6 Hz, 2H), 2.79 (s, 3H), 1.51 (s, 9H).

9-Fluoro-3,4-dihydro-1H-[1,4]diazepino[6,7,1-hi]indole-2-carboxylic acid tert-butyl ester Add sodium hydride (60%) (666 mg, 16.65 mmol) in one portion to a solution of methanesulfonic acid 2-[tert-butoxycarbonyl-(5-fluoro-1H-indol-7-ylmethyl)-amino]-ethyl ester (5.9 g, assume 15.14 mmol) in dimethylformamide (40 mL) at 0° C. Stir the reaction mixture at 0° C. for 10 minutes and then at room temperature for 30 minutes. Add water (200 mL) slowly. Filter and dry the resulting yellow precipitate to provide the desired compound (4.14 g, 94%).

$^1$H-NMR (300 MHz, CDCl$_3$): δ 7.15 (d, J=9.1 Hz, 1H), 7.07 (s, 1H), 6.78 (dd, J=14.7, 8.8 Hz, 1H), 6.49 (d, J=3.1 Hz, 1H), 4.81 (s, 1H), 4.76 (s, 1H), 4.25-4.23 (m, 2H), 3.94-3.83 (m, 2H), 1.49 (s, 9H).

9-Fluoro-7-methoxyoxalyl-3,4-dihydro-1H-[1,4] diazepino[6,7,1-hi]indole-2-carboxylic acid tert-butyl ester Add oxalyl chloride (1.62 mL, 18.56 mmol) to a solution of 9-fluoro-3,4-dihydro-1H-[1,4]diazepino[6,7,1-hi]indole-2-carboxylic acid tert-butyl ester (4.14 g, 14.28 mmol) in methyl tert-butyl ether (100 mL) at −5° C. Warm the reaction mixture to room temperature over 1.5 hours and then cool to −5° C. Add methanol (11.6 mL, 286 mmol) and stir at −5° C. for 30 minutes. Add saturated aqueous sodium bicarbonate (100 mL) and extract with ethyl acetate (100 mL×3). Wash the combined organic phase sequentially with saturated aqueous sodium bicarbonate (200 mL×3) and saturated aqueous sodium chloride (200 mL×2). Dry the organic phase over sodium sulfate and then concentrate under reduced pressure to provide the title compound as a yellow solid (5.13 g, 93%).

$^1$H-NMR (300 MHz, CDCl$_3$): δ 8.38 (s, 1H), 8.04 (d, J=6.8 Hz, 1H), 6.89 (dd, J=19.7, 8.6 Hz, 1H), 4.90 (s, 1H), 4.81 (s, 1H), 4.45-4.43 (m, 2H), 4.05-3.93 (m, 2H), 3.95 (s, 3H), 1.42 (s, 9H).

Preparation 3

3-(9-Fluoro-1,2,3,4-tetrahydro-[1,4]diazepino[6,7,1-hi] indol-7-yl)-4-imidazo[1,2-a]-pyridin-3-yl-pyrrole-2,5-dione dihydrochloride Add potassium tert-butoxide (4.58 g, 40.92 mmol) in one portion to a solution of 9-fluoro-7-methoxyoxalyl-3,4-dihydro-1H-[1,4]diazepino[6,7,1-hi]indole-2-carboxylic acid tert-butyl ester (5.13 g, 13.64 mmol) and 2-imidazo[1,2-a] pyridin-3-yl-acetamide (2.39 g, 13.64 mmol) in dimethylformamide (80 mL). Stir the reaction mixture at room temperature for three hours. Add saturated aqueous ammonium chloride (200 mL) and extract with ethyl acetate (200 mL×3). Wash the combined organic phases with saturated aqueous sodium chloride (200 mL×3), dry over sodium sulfate, and concentrate under reduced pressure. Dissolve the residue in dichloromethane (20 mL) and add 4N HCl in dioxane (40 mL) drop wise, then stir at room temperature for 4 hours. Filter the resulting precipitate and wash with diethyl ether to provide the title compound as a red solid (4.4 g, 68%).

MS (APCI): m/z=402 [C$_{22}$H$_{16}$FN$_5$O$_2$+H]$^+$.

EXAMPLE 1

7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine Add piperidine-1-carbonyl chloride (0.5 mL, 4.0 mmol) to a solution of 3-(9-fluoro-1,2,3,4-tetrahydro-[1,4]diazepino [6,7,1-hi]indol-7-yl)-4-imidazo[1,2-a]pyridin-3-yl-pyrrole-2,5-dione (1.42 g, 3.0 mmol) and triethylamine (2.09 mL, 15.0 mmol) in methanol (80 mL). Stir at room temperature over night. Add triethylamine (1.04 mL, 7.5 mmol) and piperidine-1-carbonyl chloride (0.5 mL, 4.0 mmol). Stir at room temperature for 5 hours. Add ethyl acetate (500 mL) and wash sequentially with saturated aqueous sodium bicarbonate (300 mL×3) and saturated aqueous sodium chloride (200 mL). Dry the organic phase over sodium sulfate and concentrate under reduced pressure. Subject the residue to silica gel chromatography, eluting with 0% to 3% methanol in ethyl acetate to provide the title compound as a red solid (700 mg, 45%).

m.p.=188-190° C.

MS (APCI): m/z=513 [C$_{28}$H$_{25}$FN$_6$O$_3$+H]$^+$.

EXAMPLE 2

7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine methanesulfonate Heat a slurry of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine (500 mg, 0.976 mmol) in methanol (2.5 mL) to 64° C. Add a solution of methanesulfonic acid (64 µL, 0.976 mmol) in methanol (1.0 mL) over 5 minutes. Stir the mixture at 64° C. for 15 minutes and then add isopropanol (5.0 mL) over 30 minutes. Allow the resulting slurry to cool to room temperature over 1 hour and then stir at room temperature for 4 hours. Filter the slurry, wash with isopropanol, and dry under reduced pressure at 42° C. to provide the title compound as an orange solid (478 mg, 88.5% (adjusted for 9.9% volatiles in starting material and 1.0% volatiles in product)).

m.p.=282.3° C. (DSC)

EXAMPLE 3

7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine ethanolate Heat a slurry of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine (2.0 g, 3.9 mmol) in ethanol (30 mL) to 70° C. Add 5M HCl (0.73 mL) all at once. Stir the mixture at 70° C. for 10 minutes and then add 1N NaOH (3.63 mL) over 3 minutes. Stir the mixture at 70° C. for 2 hours. Allow the resulting slurry to cool to room temperature over 1 hour and then stir at room temperature for 3.5 hours. Filter the slurry, wash with ethanol, and dry under reduced pressure at 42° C. to provide the title compound as an orange solid (1.84 g, 92% (adjusted for 7.5% volatiles in starting material and 7.7% volatiles in product)).

m.p.=179.4° C. (DSC)

Powder X-ray Principal Peaks (Degrees 2 Theta, Intensity): 8.989°, 100%; 9.787°, 48.7%; 12.846°, 20.0%; and 7.444°, 17.5%.

EXAMPLE 4

7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine hydrate I Heat a slurry of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine ethanolate (198.5 mg) in water (10 mL) to 80° C. for 2.75 hours. Add 3.11 mL of 1N HCl. When the temperature has returned to 80° C., rapidly add 3.11 mL of 1N NaOH. Allow the temperature to remain at 80° C. for approximately 15 minutes then allow the suspension to cool to room temperature. Collect the solid using vacuum filtration through Whatman #1 paper and allow to dry loosely covered over night. Powder X-ray Principal Peaks (Degrees 2 Theta, Intensity): 12.089°, 100%; 10.485°, 83.6%; 13.227°, 56.0%; and 7.660°, 8.0%.

EXAMPLE 5

7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine hydrate II Heat a slurry of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine ethanolate (200.6 mg) in water (25 mL) to 75° C. for 0.5 hours. Add 0.72 mL of 1N HCl and continue to heat for 0.75 hours. Rapidly add 0.72 mL of 1N NaOH. Allow the suspension to cool to room temperature. Collect the solid using vacuum filtration through Whatman #1 paper, rinse with 20 mL deionized water and allow to dry loosely covered for 2 days.

Powder X-ray Principal Peaks (Degrees 2 Theta, Intensity): 6.878°, 100%; 5.732°, 58.7%; 11.550°, 82.8%; 18.426°, 20.7%; and 10.856°, 44.2%.

EXAMPLE 6

7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine dihydrate Heat a slurry of 7-(2,5-dihydro-4-imidazo[1,2-a]pyridine-3-yl-2,5-dioxo-1H-pyrrol-3-yl)-9-fluoro-1,2,3,4-tetrahydro-2-(1-piperidinyl-carbonyl)-pyrrolo[3,2,1-jk][1,4]benzodiazepine ethanolate (200.8 mg) in water (25 mL) to 75° C. for 0.67 hours. Add 0.72 mL of 1N HCl and continue to heat for 1.75 hours. Add 0.1N NaOH in 1 mL increments every 5 minutes until 7.2 mL have been added. After the last addition, allow the suspension to remain at 75° C. for 0.67 hours and then allow the suspension to cool to room temperature. Collect the solid using vacuum filtration through Whatman #1 paper, rinse with 20 mL deionized water and allow to dry loosely covered for 2 days.

Powder X-ray Principal Peaks (Degrees 2 Theta, Intensity): 5.498°, 100%; 22.149°, 100%; 14.921°, 32.9%; 11.399°, 36.7%; and 11.019°, 20.5%.

Compound 1 is preferably formulated as a pharmaceutical composition prior to administration to a patient. Useful formulations comprise Compound 1 or a pharmaceutically acceptable salt or solvate thereof and SBE7-β-CD. The compound SBE7-β-CD is a sulfobutyl ether of β-cyclodextrin described in U.S. Pat. No. 5,134,127. It is sold under the trade name CAPTISOL®. Particular formulations are described in the following Formulation Examples.

A useful pharmaceutical composition may be prepared by dissolving Compound 1 or a pharmaceutically acceptable salt or solvate thereof (50 mg/mL) in 2-pyrrolidone (SOLUPHOR®-P). This solution is then diluted with an aqueous solution of SBE7-β-CD (30% by volume) and poloxamer 188 (Lutrol®-F 68) (10% by volume).

FORMULATION EXAMPLE 1

Prepare a first solution by adding 30.0 g SBE7-β-CD to 71.25 mL of water and stir or agitate until completely dissolved. Add 10.0 g poloxamer 188 and continue stirring until completely dissolved. Prepare a second solution by adding Compound 1 ethanolate to 2-pyrrolidone according to the following formula: mL 2-pyrrolidone=(actual Compound 1 ethanolate wt (mg)/50 mg/mL)×0.5. Add the first solution to the second solution. Filter the resulting solution through a 0.2 µm SUPOR® (hydrophilic polyethersulfone) filter (Pall Corporation) into a dust free container.

A further pharmaceutical composition embodiment is prepared by combining Compound 1 or a pharmaceutically acceptable salt or solvate thereof in an equimolar amount of a pharmaceutically acceptable acid in water. This mixture is then combined with at least one molar equivalent of SBE7-β-CD as an aqueous solution. Preferred pharmaceutically acceptable acids include HCl, HBr, sulfuric acid and methanesulfonic acid. The use of HCl is especially preferred.

FORMULATION EXAMPLE 2

Prepare a first solution by adding 20.0 g SBE7-β-CD to 80.0 mL of water and stir or agitate until completely dissolved. Add this solution to Compound 1 ethanolate according to the following formula: mL of first solution=(actual Compound I ethanolate wt (mg)/20 mg/mL)−(actual Compound 1 ethanolate wt (mg)/1200 mg/mL)−(actual Compound 1 ethanolate wt (mg)×0.00195107 mL of 1N HCl/mg Compound 1 ethanolate). Add 1N HCl according to the following calculation: mL of 1N HCl to add=(actual Compound 1 ethanolate wt (mg)×0.00195107 mL of 1N HCl/mg Compound 1 ethanolate). Stir or bath sonicate until all compound has dissolved.

A preferred pharmaceutical composition embodiment is prepared by adding 1 molar equivalent of Compound 1 or a pharmaceutically acceptable salt or a solvate thereof to an aqueous solution of at least 1 molar equivalent of SBE7-β-CD at a pH below 5.5 (initial solution pH), optionally in the presence of a pharmaceutically acceptable buffer, and mixing until the Compound 1 or a pharmaceutically acceptable salt or solvate thereof has dissolved. The pH is then adjusted to between 2.5 and 3.5 with a pharmaceutically acceptable base (final solution pH). This resulting solution formulation may be administered to a patient directly, or the solution may preferably be lyophilized to provide a solid formulation capable of reconstitution with water.

The SBE7-β-CD may be present in the range of 1 molar equivalent up to an amount required to administer no more than 13.4 gm of SBE7-β-CD to a patient in a day. A preferred amount of SBE7-β-CD is from 1.0 to 4.0 molar equivalents, more preferred is from 2.0 to 3.0 molar equivalents, and from 2.5 to 2.7 molar equivalents relative to Compound I is especially preferred.

Although any initial solution pH below 5.5 is acceptable, an initial solution pH below 3.0 is preferred, an initial solution pH in the range of 1.0 to 2.0 is more preferred, and an initial solution pH of between 1.2 and 1.4 is most preferred. The target initial solution pH is achieved by the addition of any pharmaceutically acid capable of adjusting the pH of the solution to a pH less than 5.5. The use of hydrochloric acid is preferred.

The formulation may optionally contain a pharmaceutically acceptable buffer. Pharmaceutically acceptable buffers are those compounds employed by one skilled in the pharmaceutical formulation arts to stabilize the pH of a final solution in a particular pH range. Pharmaceutically acceptable buffers include phosphate buffers as well as citric acid, glycine, and tartaric acid or pharmaceutically acceptable salts thereof. Pharmaceutically acceptable salts of these acids include the sodium and potassium salts. It is preferred that a pharmaceutically acceptable buffer is present in the formulation. Tartaric acid is a preferred pharmaceutically acceptable buffer.

It is important that the Compound 1 dissolve completely before the pH is adjusted to the final solution pH. Dissolution may be assisted by any mechanical mixing means or by adjusting the temperature of the solution if necessary or desired. Stirring the solution at room temperature is preferred.

The final solution pH is achieved by the addition of any pharmaceutically acceptable base capable of adjusting the pH of the solution to a pH in the range of 2.5 to 3.5. The use of sodium hydroxide is preferred. The final solution pH may be in the range of 2.5 to 3.5, but is preferably in the range of 2.5 to 3.1. A final solution pH in the range of 2.7 to 3.1 is most preferred. Once the final solution pH has been achieved, the solution may be lyophilized if necessary or desired under standard lyophilization conditions to provide a solid pharmaceutical composition suitable for reconstitution with water.

FORMULATION EXAMPLE 3

Prepare a solution of 0.15 g tartaric acid and 12 g (5.55 mmol) SBE7-β-CD in 70 mL of water. Add 5 mL of 1.0 N HCl and mix at room temperature. Add 1.1 g (2.15 mmol) Compound 1 ethanolate and stir at room temperature until dissolved. Add 1N sodium hydroxide to a pH of about 2.9. Add sufficient water to achieve a final volume of 100 mL. Lyophilize this solution to provide an amorphous orange-red solid.

I claim:

1. A method of treating a patient suffering from a non-mixed lineage leukemia based chronic myeloproliferative disorder which is acute myelogenous leukemia comprising administering to a patient in need of treatment an effective amount of 7-(2,5-dihydro-4-imidazo[1,2-a]pyridine-3-yl-2,5-dioxo-1H-pyrrol-3-yl)9-fluoro-1,2,3,4-tetrahydro-2-(1-piperidinylcarbonyl)-pyrrolo[3,2,1-jk][1,4]benzodiazepine or pharmaceutically acceptable salt or solvate thereof.

* * * * *